(12) United States Patent
Conlon et al.

(10) Patent No.: US 7,422,903 B2
(45) Date of Patent: Sep. 9, 2008

(54) MULTI-ANALYTE REFERENCE SOLUTIONS

(75) Inventors: Dennis Robert Conlon, Shirley, MA (US); Sohrab Mansouri, Sudbury, MA (US); Giannantonio Vago, Casatenovo (IT)

(73) Assignee: Instrumentation Laboratory Company, Lexington, MA (US)

( * ) Notice: Subject to any disclaimer, the term of this patent is extended or adjusted under 35 U.S.C. 154(b) by 924 days.

(21) Appl. No.: 10/733,871

(22) Filed: Dec. 11, 2003

(65) Prior Publication Data

US 2004/0209371 A1 Oct. 21, 2004

Related U.S. Application Data

(60) Provisional application No. 60/432,373, filed on Dec. 11, 2002.

(51) Int. Cl.
*G01N 31/00* (2006.01)
*G01N 33/96* (2006.01)

(52) U.S. Cl. ............... 436/8; 436/11; 436/14; 436/16; 436/18; 436/63; 436/70; 252/408.1

(58) Field of Classification Search .......... 436/8, 436/10, 11, 14, 15, 16, 18; 252/408.1
See application file for complete search history.

(56) References Cited

U.S. PATENT DOCUMENTS

| | | | |
|---|---|---|---|
| 3,658,478 A | 4/1972 | Spergel et al. | |
| 3,723,281 A | 3/1973 | Wise | |
| 3,796,634 A | 3/1974 | Haynes et al. | |
| 3,915,829 A | 10/1975 | Krebs | |
| 3,920,580 A * | 11/1975 | Mast | 436/14 |
| 3,977,995 A | 8/1976 | Louderback et al. | |
| 4,179,349 A | 12/1979 | Park | |
| 4,188,465 A | 2/1980 | Schneider et al. | |
| 4,214,968 A | 7/1980 | Battaglia et al. | |
| 4,219,440 A | 8/1980 | Runck et al. | |
| 4,271,474 A | 6/1981 | Belanger et al. | |
| 4,355,105 A | 10/1982 | Lantero, Jr. | |
| 4,361,539 A | 11/1982 | Weinberg et al. | |
| 4,390,627 A | 6/1983 | Lantero, Jr. | |
| 4,401,548 A | 8/1983 | Brezinski | |

(Continued)

FOREIGN PATENT DOCUMENTS

EP     0 094 677     11/1983

(Continued)

OTHER PUBLICATIONS

Ohboshi et al. "Usefulness of polyethylene glycol for cryopreservation by vitrification of in vitro-derived bovine blastocysts" *Animal Reproduction Science*, (1997) 27-36.

(Continued)

*Primary Examiner*—Maureen M Wallenhorst
(74) *Attorney, Agent, or Firm*—K&L Gates LLP

(57) ABSTRACT

The present invention provides a reference solution for use in instruments that determine hematocrit levels in biological samples by measuring the resistance and/or conductivity of the biological samples. A reference solution according to the invention achieves conductivities representative of known hematocrit levels in blood, while maintaining tolerable levels of interference with the measurement of other analytes in the reference solution.

30 Claims, 5 Drawing Sheets

U.S. PATENT DOCUMENTS

| | | |
|---|---|---|
| 4,431,507 A | 2/1984 | Nankai et al. |
| 4,481,804 A | 11/1984 | Eberhard et al. |
| 4,551,482 A | 11/1985 | Tschang et al. |
| 4,654,127 A | 3/1987 | Baker et al. |
| 4,670,127 A | 6/1987 | Ritter et al. |
| 4,686,479 A | 8/1987 | Young et al. |
| 4,713,165 A | 12/1987 | Conover et al. |
| 4,734,184 A | 3/1988 | Burgess et al. |
| 4,755,461 A | 7/1988 | Lawson et al. |
| 4,760,024 A | 7/1988 | Lantero, Jr. |
| 4,810,351 A | 3/1989 | Chapoteau et al. |
| 4,818,361 A | 4/1989 | Burgess et al. |
| 4,818,365 A | 4/1989 | Kinlen et al. |
| 4,871,439 A | 10/1989 | Enzer et al. |
| 4,908,117 A | 3/1990 | Kinlen et al. |
| 4,936,975 A | 6/1990 | Shibata et al. |
| 4,945,062 A | 7/1990 | Chiang |
| 4,950,378 A | 8/1990 | Nagata |
| 4,973,394 A | 11/1990 | Ross et al. |
| 4,975,647 A | 12/1990 | Downer et al. |
| 5,013,666 A | 5/1991 | Chiang |
| 5,061,631 A | 10/1991 | Calabrese |
| 5,067,093 A | 11/1991 | Przybylowicz et al. |
| 5,070,023 A | 12/1991 | Calabrese |
| 5,103,179 A | 4/1992 | Thomas et al. |
| 5,132,345 A | 7/1992 | Harris et al. |
| 5,162,077 A | 11/1992 | Bryan et al. |
| 5,200,051 A | 4/1993 | Cozzette et al. |
| 5,212,050 A | 5/1993 | Mier et al. |
| 5,262,305 A | 11/1993 | Heller et al. |
| 5,286,364 A | 2/1994 | Yacynych et al. |
| 5,326,449 A | 7/1994 | Cunningham |
| 5,330,634 A | 7/1994 | Wong et al. |
| 5,338,435 A | 8/1994 | Betts et al. |
| 5,342,498 A | 8/1994 | Graves et al. |
| 5,352,349 A | 10/1994 | Inamoto et al. |
| 5,370,783 A | 12/1994 | Carlson et al. |
| 5,387,329 A | 2/1995 | Foos et al. |
| 5,403,451 A | 4/1995 | Riviello et al. |
| 5,405,510 A | 4/1995 | Betts et al. |
| 5,411,647 A | 5/1995 | Johnson et al. |
| 5,505,828 A | 4/1996 | Wong et al. |
| 5,540,828 A | 7/1996 | Yacynych |
| 5,541,097 A | 7/1996 | Lantero et al. |
| 5,558,985 A | 9/1996 | Chiang et al. |
| 5,605,837 A | 2/1997 | Karimi et al. |
| 5,653,862 A | 8/1997 | Parris |
| 5,705,482 A | 1/1998 | Christensen et al. |
| 5,780,302 A | 7/1998 | Conlon et al. |
| 5,798,030 A | 8/1998 | Raguse et al. |
| 5,849,517 A * | 12/1998 | Ryan ................. 435/40.51 |
| 5,972,199 A | 10/1999 | Heller et al. |
| 6,030,827 A | 2/2000 | Davis et al. |
| 6,051,389 A | 4/2000 | Ahl et al. |
| 6,123,820 A | 9/2000 | Bergkuist et al. |
| 6,133,229 A | 10/2000 | Gibson et al. |
| 6,136,607 A | 10/2000 | Conlon et al. |
| 6,136,960 A * | 10/2000 | Chait et al. ................ 530/412 |
| 6,143,545 A | 11/2000 | Clausen et al. |
| 6,174,728 B1 | 1/2001 | Ben-David et al. |
| 6,200,947 B1 | 3/2001 | Takashima et al. |
| 6,214,185 B1 | 4/2001 | Offenbacher et al. |
| 6,251,684 B1 * | 6/2001 | Buhl et al. ................ 436/166 |
| 6,337,189 B1 * | 1/2002 | Ryan ................. 435/40.5 |
| 6,413,396 B1 | 7/2002 | Yang et al. |
| 6,478,950 B1 | 11/2002 | Peat et al. |
| 6,482,416 B2 | 11/2002 | Munn et al. |
| 6,531,317 B2 * | 3/2003 | Guirguis et al. ............ 436/18 |
| 6,652,720 B1 | 11/2003 | Mansouri et al. |
| 6,872,297 B2 | 3/2005 | Mansouri et al. |
| 7,022,219 B2 | 4/2006 | Mansouri et al. |

FOREIGN PATENT DOCUMENTS

| | | |
|---|---|---|
| EP | 0 125 136 | 11/1984 |
| EP | 0 133 531 | 2/1985 |
| EP | 0 138 150 A2 | 4/1985 |
| EP | 0 362 032 | 4/1990 |
| EP | 0 388 017 | 9/1990 |
| EP | 0 654 664 A2 | 5/1995 |
| EP | 0 771 867 | 5/1997 |
| EP | 0 772 041 | 5/1997 |
| EP | 0 872 726 | 10/1998 |
| EP | 0 909 952 | 4/1999 |
| FR | 2792726 | 10/2000 |
| GB | 2194843 | 3/1988 |
| JP | 60155959 | 8/1985 |
| JP | 01028555 | 1/1989 |
| WO | 93/21533 | 10/1993 |
| WO | WO 94/06019 | 3/1994 |
| WO | 94/19683 | 9/1994 |
| WO | 94/19684 | 9/1994 |
| WO | 97/15827 | 5/1997 |
| WO | WO 01/42473 | 6/2001 |
| WO | 01/65248 | 9/2001 |
| WO | 02/097419 A1 | 12/2002 |
| WO | 04/072606 A2 | 8/2004 |

OTHER PUBLICATIONS

Varlan et al. "New design technique for planar conductometric haematocrit sensors" *Sensors and Actuators B*, (1996), 258-264.

Wang et al. "Cryopreservation of *Musca domestica* (Diptera: Muscidae) Embryos" *Cryobiology*, (2000), 153-166.

International Search Report for Application No. PCT/US03/39411 dated Jun. 29, 2004.

Andersson et al., "Protein Stabilising Effect of Polyethyleneimine," *Journal of Biotechnology*, 72, 21-31 (1999).

Baraona et al., "Effects of Alcohol and Polyenylphosphatidylcholine on Hepatic Nitric Oxide Production and its Peroxynitrite-Mediated Toxicity," *Alcoholism Clinical and Experimental Research*, 24:5 Supplement, 200A (2000) (Abstract only).

Bentley et al., "Activation of Superoxide Production and Differential Exocytosis in Polymorphonuclear Leukocytes by Cytochalasins A, B, C, D and E: Effects of Various Ions," *Biochimica et Biophysica Acta*, 678, 238-44 (1981).

Bott, Adrian W., "Electrochemical Methods for the Determination of Glucose," *Current Separations*, 17:1, 25-31 (1998).

Buono et al., "Blood lactate and ammonium ion accumulation during graded exercise in humans," *Journal of Applied Physiology: Respiratory, Environmental and Exercise Physiology*, 57:1, 135-9 (1984).

Cao et al., "Enhancing Enzymatic Properties by the Information Method," *Applied Biochemistry and Biotechnology*, 59:1, 7-14 (1996).

Castillo et al., "Effect of an acute oral load of magnesium on blood glucose and plasma insulin levels in healthy subjects," *Advances in Magnesium Research*, 1(Magnesium in Cardiology), 197-203 (1997) (Abstract only).

Chen et al., "Stability of Oxidases Immobilized in Silica Gels," *J. Am. Chem. Soc.*, 120, 4582-4585 (1998).

Cho et al., "Effects of Choline Chloride and its Analogues on Photosynthesis in Wheat Protoplasts," *Proceedings of the Fourteenth Annual Plant Growth Regulator Society of America Meeting*, 131-34 (1987).

Cosofret et al., "Electroanalytical and Biocompatibility Studies on Carboxylated Poly(vinyl chloride) Membranes for Microfabricated Array Sensors," *Analyst*, 119, 2283-2292 (1994).

Dehlawi et al, "Choline Derivatives and Sodium Fluoride Project Acetylcholinesterase against Irreversible Inhibition and Aging by DFP and Paraoxon," *Journal of Biochemical Toxicology*, 9:5, 261-268 (1994).

Emnéus et al., "Comparison Between Different Inorganic Supports for the Immobilization of Amyloglucosidase and α-amylase to Be Used in Enzyme Reactors in Flo-Injections Systems," *Analytica Chimica Acta*, 276, 303-318 (1993).

Enami, "Effects of Phenyl N-*tert*-Butyl Nitrone and its Derivatives on Hepatocarcinogenesis in Rats Fed a Choline-Deficient, L-Amino Acid-Defined Diet," *Journal of Nara Medical Association*, 51:6, 468-482 (2000), (English abstract attached).

Erecińska, "Stimulation of the NA+/K+ Pump Activity During Electrogenic Uptake of Acidic Amino Acid Transmitters by Rat Brain Synaptosomes," *Journal of Neurochemistry*, 52, 135-139 (1989).

Evers et al., "The influence of intravenous magnesium administration on cerebral blood flow," *Advances in Magnesium Research*, 1(Magnesium in Cardiology), 233-237 (1997).

Farombi et al., "Antioxidant activity of palm oil carotenes in organic solution: effects of structure and chemical reactivity," *Food Chemistry*, 64:3, 315-321 (1999).

Farombi et al., "Antioxidant activity of palm oil carotenes in peroxyl radical-mediated peroxidation of phosphatidyl choline liposomes," *Redox Report*, 4:1/2, 61-68 (1999).

Farombi et al., "Evaluation of the Antioxidant activity and partial characterisation of extracts from browned yam flour diet," *Food Research International*, 33:6, 493-499 (2000).

Garcia et al., "An Immobilization Technique Yielding High Enzymatic Load on Nylon Nets," *Biotechnology Techniques*, 4:6, 425-428 (1990).

Geise et al., "Electropolymerized Films to Prevent Interferences and Electrode Fouling in Biosensors," *Biosensors & Bioelectronics*, 6, 151-160 (1991).

Ghindilis et al., "Glucose Potentiometric Electrodes Based on Mediatorless Bioelectrocatalysis. A New Approach," *Biosensors & Bioelectronics*, 9, 353-357 (1994).

Ghoshal et al., "Prevention by Free Radical Scavenger $AD_5$ of Prooxidant Effects of Choline Deficiency," *Free Radical Biology & Medicine*, 8, 3-7 (1990).

Grattagliano et al., "Starvation Impairs Antioxidant Defense in Fatty Livers of Rats Fed A Choline-Deficient Diet[1]," *The Journal of Nutrition*, 130:9, 2131-2136 (2000).

Grolier Multimedia Encyclopedia definition of "sodium pentothal" downloaded Dec. 3, 2005.

Grolier Multimedia Encyclopedia definition of "ibuprofen" downloaded Dec. 3, 2005.

Hart et al., "Estimation of Lactate in Meat Extracts by Screen-Printed Sensors," *Analytical Chimica Acta*, 386, 7-12 (1999).

Heller et al., "Loss of Activity or Gain in Stability of Oxidases Upon Their Immobilization in Hydrated Silica: Significance of the Electrostatic Interactions of Surface Arginine Residues at the Entrances of the Reaction Channels," *J. Am. Chem. Soc.*, 120, 4586-4590 (1998).

Hiramatsu et al., "Free radicals, lipid peroxidation, SOD activity, neurotransmitters and choline acetyltransferase activity in the aged rat brain," *Free Radicals and Aging*, 213-218., 1992.

Huntsman et al., "Nucleus-Specific Differences in $GABA_A$-Receptor-Mediated Inhibition Are Enhanced During Thalamic Development," *The American Physiological Society*, 350-358 (2000).

Ikariyama et al., Polypyrrole Electrode as a Detector for Electroinactive Anions by Flow Injection Analysis, *Anal. Chem.*, 58, 1803-1806 (1986).

Jürgens et al., "Delay of copper-catalyzed oxidation of low density lipoprotein by in vitro enrichment with choline or ethanolamine plasmalogens," *Chemistry and Physics of Lipids*, 77:1, 25-31 (1995).

Katsu et al., "Organic ammonium ion-selective electrodes using acyclic neutral carriers developed for inorganic cation-selective electrodes," *Analytical Sciences* 16:5, 523-525 (2000) (Abstract only).

Kaul et al., "Plant Polyphenols Inhibit Benzoyl Peroxide-Induced Superoxide Anion Radical Production and Diacylglyceride Formation in Murine Peritoneal Macrophages," *Nutrition and Cancer*, 35:2, 207-211 (1999).

Kruk, "The use of biologically active substances in the freezing of boar semen," *Zootekhniya*, 10, 28-30 (1996) (English abstract attached.).

Lim et al., "Gas Permeable Membranes Composed of Carboxylated Poly(vinyl chloride) and Polyurethane," *Bull Korean Chem. Soc.*, 20, 672-76 (1999).

Lima et al., "Dopamine Ion-Selective Electrode for Potentiometry in Pharmaceutical Preparations," *Mikrochim. Acta*, 131, 187-191 (1999).

Lindner et al., "Responses of H+Selective Solvent Polymeric Membrane Electrodes Fabricated From Modified PVC Membranes," *Talanta*, 40:7, 957-967 (1993).

Lingane, "Common Electrical Measurements," *Electroanalytical Chemistry* (2nd Ed.), Interscience Publishers, Inc., New York, 26-29 (1958).

Lingane, "Controlled Potential Methodology," *Electroanalytical Chemistry* (2nd Ed.), Interscience Publishers, Inc., New York, 358-365 (1958).

Lippman, "The Prolongation of Life: A Comparison of Antioxidants and Geroprotectors Versus Superoxide in Human Mitochondria," *Journal of Gerontology*, 36:5, 550-557 (1981).

Lipták et al. (eds.), "Ion Selective Electrodes," *Instrument Engineers' Handbook*, Chilton Book Co., Radnor, Pennsylvania, 655-703 (1982).

Mádáras et al., "Miniaturized Biosensors Employing Electropolymerized Permselective Films and Their Use for Creatinine Assays in Human Serum," *Anal. Chem.*, 68, 3832-3839 (1996).

Mansouri et al., "Development of a Glucose Sensor and Its Inclusion in the GEM Blood Analyzer," *International Federation of Clinical Chemistry and Laboratory Medicine*, 368-377 (1998).

Meyer et al., "Effects of Peroxidation and Aging on Rat Neocortical ACh-Release and Protein Kinase C," *Neurobiology of Aging*, 15:1, 63-67 (1994).

Minagawa et al., "Development of Long Life Lactate Sensor Using Thermostable Mutant Lactate Oxidase," *Biosensors and Bioelectronics*, 13:3-4, 313-318 (1998).

Moody et al., "PVC Matrix Membrane Ion-Selective Electrodes," *J. Chem Educ.*, 51: 541-44 (1974).

Mueller et al., "Magnesium selective electrodes for blood serum studies and water hardness measurements," *Mikrochimica Acta*, 3:1-6, 283-90 (1988) (Abstract only).

Nakae et al., "Preventive Effects of Various Antioxidants on Endogenous Liver Carcinogenesis in Rats Fed a Choline-Deficient, L-Amino Acid-Defined Diet," *Food Factors for Cancer Prevention*, 92-97, date unknown.

O'Donnell et al., "Development of magnesium-selective ionophores," *Analytica Chimica Acta*, 281:1, 129-34 (1993).

Oh et al., "Potassium-Selective PVC Membrane Electrodes Based on Newly Synthesized *cis*- and *trans*- Bis(crown ether)s," *Anal.Sci.*, 14, 1009-12 (Oct. 1998).

Patel et al., "Fabrication and Characterization of Disposable Type Lactate Oxidase Sensors for Dairy Products and Clinical Analysis," *Sensors and Actuators*, B 67, 134-141 (2000).

Petersson, "Enzymic determination of urea in undiluted whole blood by flow-injection analysis using an ammonium ion-selective electrode," *Analytica Chimica Acta*, 209:1-2, 239-48 (1988).

Phung et al., "Role of Antioxidants in Inhibiting Hepatic Fibrosis in a Murine Nutritional Model of Nash, *Hepatology*," 32:4, 168 (Abstract only), date unknown.

"Reference Electrodes," http://www.epsilon-web.com/Ec/manual/Maintenance/reference.html (printed on Feb. 23, 2001).

Saito et al., "Antioxidant Activity and Active Sites of Phospholipids and Antioxidants," *Journal of the American Oil Chemists' Society*, 74:12, 1531-1536 (1997).

Sasso et al., "Electropolymerized 1, 2-Diaminobenzene as a Means to Prevent Interferences and Fouling and To Stabilize Immobilized Enzyme in Electrochemical Biosensors," *Analytical Chemistry*, 62:11, 1111-1117 (1990).

Shin et al., "Potentiometric biosensors using immobilized enzyme layers mixed with hydrophilic polyurethane,"*Sensors and Actuators*, 19-26 (1998).

Singer et al., "The significance of blood urea and acidosis in the prognosis of chronic Kidney disease," *Kiln. Wochschr,*, 9, 440-1 (1930).

Spichiger, "History of the development of magnesium-selective ionophores and magnesium-selective electrodes," *Electroanalysis*, 5:9-10, 739-45 (1993) (Abstract only).

Suzuki et al., "Microfabricated Liquid Junction Ag/AgCI Reference electrode and Its Application to a One-Chip Potentiometric Sensor," *Anal. Chem.*, 71, 5069-5075 (1999).

Umezawa et al., "Potentiometric Selectivity Coefficients of Ion-Selected Electrodes: Part 1. Inorganic Cations," *Pure Appl. Chem.*, 72, 1851-56 (2000).

Waser, "Quantitative Chemistry: A Laboratory Test," *W.A. Benjamin, Inc., New York*, 41, 117-119, 207-208, 213-214, 223 (1961).

West et al., "Proton translocation by cytochrome oxidase in (antimycin +myxothiazol)-treated rat liver mitochondria using ferrocyanide or hexammineruthenium as electron donor," *Biochemistry Journal*, 236:1, 15-21 (1986).

Williams et al., "Cerebral Microvessel Phospholipase $A_2$ Activity in Senescent Mouse," *Neurochemical Research*, 19:3, 317-320 (1994).

Wilson et al., "Protection by Antioxidants Against Arterial Sclerosis of Chronic Choline-Deficiency," *Experimental and Molecular Pathology*, 21, 118-122 (1974).

Wilson et al., "Vascular Damage and Lipid Peroxidation in Choline-deficient Rats," *Experimental and Molecular Pathology*, 18:3, 357-368 (1973).

Winkler et al., "The measurement of glomerular filtration. The creatine, sucrose and urea clearances in subjects with renal disease," *Journal of Clinical Investigan*, 16, 869-77 (1937).

Wu et al., "Alzheimer's Amyloid-Beta Peptide Inhibits Sodium/Calcium Exchange Measured In Rat and Human Brain Plasma Membrane Vesicles," *Neuroscience*, 80:3, 675-684 (1997).

Wydrzynski et al., "Selective Inhibition of Photosystem II Reactions from Water Splitting to Q Reduction in Thylakoid Samples by Lauroyl Choline Chloride: Evidence from Fluorescence Transient Measurements," *Advances in Photosynthesis Research*, 1, 437-40 (1984).

Yang et al., "Needle-type Lactate Biosensor," *Biosensors and Bioelectronics*, 14, 203-221 (1999).

Partial International Search Results for International Application No. PCT/US04/002221, dated Aug. 26, 2004, 4 pages.

International Search Report for International Application No. PCT/US2004/002221 mailed Nov. 30, 2004 (7 pages).

Nova Biomedical Corp., Product Information insert for Stat Profile® pHOx® Plus L Blood Gas/$SO_2$/Hct/Hb/Electrolyte/Glucose/Lactate Auto-Cartridge QC, date unknown.

Stott, et al., "Analytical Artifacts in Hematocrit Measurements by Whole-Blood Chemistry Analyzers," Clinical Chemistry (1995), vol. 41, No. 2, pp. 306-311.

* cited by examiner

| Electrode card | pH | pCO$_2$ mmHg | pO$_2$ mmHg | Na$^+$ mmol/L | K$^+$ mmol/L | Ca$^{++}$ mmol/L | Glucose mg/dL | Lactate mmol/L | Hct % |
|---|---|---|---|---|---|---|---|---|---|
| 1 | 7.57 | 20 | 113 | 182 | 7.7 | 0.84 | 224 | 5.6 | 42 |
|   | 7.57 | 20 | 115 | 183 | 7.7 | 0.85 | 232 | 5.4 | 42 |
|   | 7.56 | 20 | 116 | 182 | 7.6 | 0.84 | 233 | 5.5 | 42 |
| 2 | 7.56 | 19 | 107 | 180 | 7.6 | 0.83 | 230 | 5.4 | 41 |
|   | 7.57 | 20 | 118 | 182 | 7.5 | 0.83 | 233 | 5.4 | 42 |
|   | 7.56 | 20 | 110 | 186 | 7.5 | 0.84 | 239 | 5.5 | 42 |
| 3 | 7.57 | 20 | 115 | 181 | 7.7 | 0.84 | 233 | 5.5 | 42 |
|   | 7.57 | 21 | 126 | 174 | 7.6 | 0.84 | 235 | 5.4 | 40 |
| 4 | 7.56 | 19 | 121 | 183 | 7.6 | 0.82 | 226 | 5.4 | 42 |
|   | 7.57 | 19 | 124 | 184 | 7.6 | 0.83 | 232 | 5.5 | 42 |
| 5 | 7.57 | 19 | 118 | 182 | 7.5 | 0.82 | 226 | 4.7 | 43 |
|   | 7.57 | 19 | 122 | 182 | 7.6 | 0.83 | 217 | 4.6 | 43 |
| 6 | 7.57 | 20 | 118 | 183 | 7.6 | 0.83 | 223 | 4.7 | 43 |
|   | 7.57 | 19 | 121 | 183 | 7.6 | 0.84 | 216 | 4.4 | 43 |
| 7 | 7.56 | 20 | 119 | 180 | 7.6 | 0.83 | 225 | 4.8 | 42 |
|   | 7.56 | 20 | 121 | 180 | 7.7 | 0.84 | 217 | 4.7 | 42 |
| 8 | 7.57 | 19 | 119 | 180 | 7.7 | 0.84 | 220 | 4.7 | 42 |
|   | 7.57 | 19 | 121 | 181 | 7.8 | 0.85 | 215 | 4.5 | 43 |
| 9 | 7.57 | 19 | 113 | 184 | 7.6 | 0.82 | 219 | 4.7 | 44 |
|   | 7.57 | 19 | 116 | 186 | 7.7 | 0.84 | 210 | 4.6 | 43 |
| 10 | 7.56 | 20 | 101 | 184 | 7.6 | 0.83 | 218 | 4.7 | 44 |
|   | 7.57 | 20 | 108 | 184 | 7.7 | 0.84 | 213 | 4.7 | 44 |
| 11 | 7.57 | 19 | 121 | 181 | 7.5 | 0.83 | 218 | 4.7 | 41 |
|   | 7.57 | 20 | 122 | 181 | 7.6 | 0.83 | 208 | 4.5 | 41 |
| 12 | 7.56 | 19 | 116 | 181 | 7.7 | 0.83 | 212 | 4.8 | 43 |
|   | 7.57 | 19 | 122 | 181 | 7.8 | 0.84 | 207 | 4.7 | 43 |
| 13 | 7.56 | 20 | 111 | 184 | 7.7 | 0.85 | 214 | 4.8 | 43 |
|   | 7.57 | 20 | 117 | 183 | 7.7 | 0.86 | 210 | 4.7 | 43 |
| 14 | 7.56 | 21 | 112 | 184 | 76 | 0.82 | 230 | 5.0 | 43 |
|   | 7.57 | 21 | 127 | 186 | 7.7 | 0.83 | 227 | 4.7 | 43 |
| 15 | 7.56 | 20 | 116 | 183 | 7.5 | 0.82 | 219 | 4.7 | 43 |
|   | 7.56 | 20 | 121 | 185 | 7.6 | 0.84 | 216 | 4.6 | 43 |
| 16 | 7.57 | 20 | 115 | 182 | 7.6 | 0.83 | 213 | 4.5 | 44 |
|   | 7.57 | 20 | 125 | 185 | 7.7 | 0.84 | 208 | 4.5 | 44 |
| 17 | 7.58 | 19 | 104 | 182 | 7.5 | 0.82 | 231 | 4.9 | 43 |
|   | 7.58 | 19 | 112 | 181 | 7.6 | 0.82 | 229 | 4.8 | 42 |
| 18 | 7.57 | 19 | 125 | 184 | 7.6 | 0.83 | 196 | 4.7 | 43 |
|   | 7.57 | 20 | 131 | 186 | 7.7 | 0.84 | 196 | 4.6 | 43 |
| 19 | 7.57 | 19 | 109 | 183 | 7.6 | 0.84 | 225 | 4.7 | 43 |
|   | 7.57 | 20 | 114 | 187 | 7.8 | 0.86 | 225 | 4.5 | 43 |
| 20 | 7.56 | 20 | 112 | 179 | 7.6 | 0.81 | 227 | 4.8 | 42 |
| 21 | 7.57 | 19 | 113 | 179 | 7.7 | 0.83 | 227 | 4.7 | 41 |
| 22 | 7.57 | 19 | 111 | 179 | 7.6 | 0.81 | 224 | 4.8 | 42 |
| 23 | 7.57 | 19 | 112 | 180 | 7.7 | 0.84 | 223 | 4.8 | 42 |
| 24 | 7.57 | 20 | 112 | 179 | 7.7 | 0.83 | 223 | 4.8 | 42 |
| 25 | 7.57 | 20 | 123 | 184 | 7.5 | 0.83 | 222 | 4.8 | 43 |
| Mean | 7.57 | 20 | 117 | 182 | 7.6 | 0.83 | 222 | 4.7 | 43 |
| Std. Dev. | 0.005 | 0.6 | 5.5 | 2.1 | 0.08 | 0.011 | 8.2 | 0.13 | 0.8 |

FIG. 3

| Time | Temp | pH | $CO_2$ | $pO_2$ | Na | K | Ca | Glu | Lac | Hct |
|---|---|---|---|---|---|---|---|---|---|---|
| 0 | N/A | 7.58 | 20 | 122 | 154 | 7.8 | 0.78 | 214 | 5.0 | 40 |
| 2 wks | 5°C | 7.58 | 21 | 120 | 154 | 7.7 | 0.79 | 215 | 5.0 | 40 |
| | 45°C | 7.56 | 22 | 107 | 154 | 7.7 | 0.78 | 213 | 5.1 | 40 |
| 4 wks | 5°C | 7.58 | 20 | 120 | 154 | 7.6 | 0.80 | 221 | 5.3 | 40 |
| | 35°C | 7.57 | 21 | 112 | 154 | 7.7 | 0.79 | 218 | 5.3 | 40 |
| | 45°C | 7.55 | 22 | 95 | 154 | 7.7 | 0.78 | 214 | 5.5 | 40 |
| 6 wks | 5°C | 7.58 | 20 | 118 | 153 | 7.5 | 0.79 | 332 | 5.2 | 40 |
| | 35°C | 7.57 | 21 | 104 | 153 | 7.4 | 0.78 | 319 | 5.3 | 40 |
| 8 wks | 5°C | 7.58 | 20 | 124 | 152 | 7.6 | 0.80 | 220 | 5.3 | 40 |
| | 35°C | 7.56 | 21 | 102 | 152 | 7.6 | 0.79 | 215 | 5.4 | 40 |
| 9 wks | 5°C | 7.58 | 20 | 124 | 152 | 7.5 | 0.80 | 222 | 5.3 | 40 |
| | 25°C | 7.58 | 20 | 120 | 152 | 7.5 | 0.79 | 219 | 5.3 | 41 |
| 13 wks | 5°C | 7.58 | 21 | 128 | 156 | 7.5 | 0.80 | 219 | 5.6 | 41 |
| | 25°C | 7.57 | 21 | 122 | 156 | 7.6 | 0.80 | 216 | 5.5 | 42 |
| 16 wks | 5°C | 7.58 | 21 | 118 | 156 | 7.5 | 0.80 | 232 | 5.6 | 41 |
| | 25°C | 7.57 | 21 | 109 | 156 | 7.6 | 0.81 | 222 | 5.5 | 41 |
| 20 wks | 5°C | 7.58 | 20 | 125 | 154 | 7.5 | 0.80 | 222 | 6.0 | 42 |
| | 25°C | 7.57 | 21 | 117 | 154 | 7.6 | 0.79 | 218 | 6.0 | 42 |

FIG. 4

| Time | Temp | pH | CO$_2$ | pO$_2$ | Na | K | Ca | Glu | Lac | Hct |
|---|---|---|---|---|---|---|---|---|---|---|
| 0 | N/A | 7.25 | 57 | 38 | 125 | 2.4 | 1.43 | 70 | 1.4 | 24 |
| 4 wks | 5°C | 7.25 | 57 | 37 | 127 | 2.4 | 1.45 | 68 | 1.3 | 24 |
|  | 25°C | 7.24 | 59 | 34 | 126 | 2.4 | 1.43 | 72 | 1.4 | 24 |
| 6 wks | 5°C | 7.25 | 56 | 38 | 126 | 2.4 | 1.42 | 74 | 1.4 | 23 |
|  | 25°C | 7.24 | 57 | 34 | 127 | 2.4 | 1.44 | 70 | 1.4 | 23 |
| 12 wks | 5°C | 7.25 | 54 | 41 | 125 | 2.4 | 1.45 | 71 | 1.6 | 23 |
|  | 25°C | 7.24 | 55 | 35 | 125 | 2.4 | 1.44 | 71 | 1.6 | 23 |

FIG. 5

| Time | Temp | pH | CO$_2$ | pO$_2$ | Na | K | Ca | Glu | Lac | Hct |
|---|---|---|---|---|---|---|---|---|---|---|
| 0 | N/A | 7.23 | 59 | 29 | 127 | 2.4 | 1.44 | 69 | 1.5 | 24 |
| 1 wk | 5°C | 7.23 | 59 | 33 | 127 | 2.4 | 1.44 | 69 | 1.5 | 23 |
|  | 45°C | 7.23 | 59 | 31 | 127 | 2.4 | 1.44 | 68 | 1.5 | 24 |
| 2 wks | 5°C | 7.23 | 58 | 29 | 127 | 2.4 | 1.44 | 70 | 1.5 | 24 |
|  | 35°C | 7.23 | 58 | 27 | 126 | 2.4 | 1.43 | 70 | 1.5 | 24 |
|  | 45°C | 7.22 | 58 | 26 | 127 | 2.4 | 1.45 | 66 | 1.4 | 24 |
| 4 wks | 5°C | 7.23 | 59 | 27 | 127 | 2.4 | 1.43 | 68 | 1.4 | 24 |
|  | 35°C | 7.23 | 60 | 25 | 127 | 2.4 | 1.43 | 68 | 1.5 | 24 |

FIG. 6

MULTI-ANALYTE REFERENCE SOLUTIONS

TECHNICAL FIELD

The present invention relates to the field of reference solutions for instruments that measure analytes in biological samples, particularly to instruments that determine hematocrit levels in biological samples by measuring the resistance and/or conductivity of the samples.

BACKGROUND INFORMATION

In the past, it was customary for clinical chemists to measure biological analytes in serum or plasma by flame photometry, coulometry, or fluorometric titration. Hematocrit, the percentage of blood volume occupied by cells (also known as packed cell volume), is measured in whole blood by microcentrifugation or cell counting. More recent advances in clinical instrumentation have allowed for simultaneous measurement of biological analytes and hematocrit in a single sample. One type of modern blood analyzer measures biological analytes (such as sodium, for example) by direct potentiometry and hematocrit by conductivity. These instruments vastly improve the speed at which hematocrit levels and the concentrations of biological analytes can be obtained, which can lead to improvements in patient diagnosis and care.

In order to confirm the accuracy of blood analyzer measurements, the instrument must be calibrated before use. Some reference solutions use blood cells or other blood products to approximate physiological hematocrit levels. However, blood products are expensive, must be refrigerated during shipment and storage, and are relatively unstable. Thus, a preferred reference solution would not contain blood products, but would still maintain a conductivity similar to a known hematocrit level.

A reference solution for biological analytes must contain known concentrations of each analyte, while a reference solution for hematocrit must have a conductivity similar to that of blood with a known hematocrit level. However, it is difficult to formulate an aqueous solution with physiological levels of biological analytes (such as sodium, for example) and hematocrit in the same solution, because an aqueous environment that lacks red blood cells is far more conductive than whole blood. Accordingly, an additive, such as inert particles or non-conductive water-soluble chemicals, must be added to achieve the necessary conductivity.

Existing reference solutions include high concentrations of conductivity-reducing additives—often up to 30-40% of the total volume of the solution—in order to achieve a conductivity representative of hematocrit levels in whole blood. However, large amounts of additives can drive up the cost of the reference solution, particularly in the case of relatively expensive inert particle additives. In addition, high concentrations of additives can lead to unwanted side-effects, including interference with other analytes in the reference solution, high viscosity, reduced shelf life, and precipitation during shipment and storage. Furthermore, certain water-soluble chemical additives can permeate some sensors within the blood analyzer (such as an oxygen sensor, for example) and reduce the sensitivity and selectivity of the sensors.

Because of these problems, existing reference solutions cannot effectively calibrate a blood analyzer for both hematocrit and biological analytes simultaneously. As a result, at least two separate reference solutions must be used to calibrate a blood analyzer, which reduces the overall speed and increases the cost of operating such instruments.

SUMMARY OF THE INVENTION

The present invention provides a reference solution for use in instruments that determine hematocrit levels in biological samples by measuring the conductivity of the biological samples. A reference solution according to the invention achieves conductivities representative of known hematocrit levels in blood, while maintaining tolerable levels of interference with the measurement of other analytes in the reference solution. In addition, a reference solution according to the invention is not highly viscous, does not form a precipitate during shipment or storage, and is more stable at room temperature than reference solutions that contain blood products. A reference solution according to the invention can be used to simultaneously calibrate an instrument that analyzes biological samples for hematocrit and biological analytes.

In general, in one aspect, the invention provides a reference solution for use in instruments that analyze biological samples that includes at least two of a water soluble polymer, a glycol, and a polysaccharide. The reference solution has a conductivity that corresponds to the conductivity of a known hematocrit level.

Embodiments of this aspect of the invention may have the following features. The water soluble polymer may be a non-ionic species, such as polyethylene glycol, for example. The glycol may be ethylene glycol. The polysaccharide may be a non-ionic species, such as dextran, for example. The water soluble polymer, glycol, and polysaccharide may be present in such amounts as to provide a solution that has a conductivity that corresponds to the known physiological hematocrit level in human blood. Alternatively, the solution may have a conductivity that is less than or greater than the known physiological hematocrit level in human blood.

The reference solution may also contain one or more analytes, which may be present in concentrations that correspond to the physiological concentrations of the analytes in human blood. The one or more analytes may be ions, such as hydrogen, sodium, potassium, calcium, chloride, bicarbonate, lithium, magnesium, and ammonium. The one or more analytes may be biological metabolites, such as glucose, lactate, urea, creatine, and creatinine. The one or more analytes may be gases, such as oxygen and carbon dioxide. Alternatively, the one or more analytes may be a mixture of ions, biological metabolites, and/or gases. The reference solution may also contain a buffer solution, a preservative, a stabilizer, a surfactant, a dye, and/or an anticoagulant. The biological sample that the instrument analyzes may be blood.

In general, in another aspect, the invention provides a reference solution for use in instruments that analyze biological samples that includes polyethylene glycol, ethylene glycol, and dextran. The reference solution has a conductivity that corresponds to the conductivity of a known hematocrit level. Embodiments of this aspect may include one or more analytes, as described above.

In general, in yet another aspect, the invention provides a reference solution for use in instruments that analyze biological samples that includes polyethylene glycol and dextran. The reference solution has a conductivity that corresponds to the conductivity of a known hematocrit level. Embodiments of this aspect may include one or more analytes, as described above.

In general, in still another aspect, the invention provides a method for calibrating an instrument that analyzes biological samples. The method involves providing a reference solution that contains at least two of a water soluble polymer, a glycol, and a polysaccharide, and has a conductivity that corresponds to the conductivity of a known hematocrit level, as described above. The reference solution is introduced to the instrument, and a signal is obtained that represents the measured conductivity value. The instrument is then adjusted so that the measured conductivity value equals the known conductivity of the reference solution.

In general, in another aspect, the invention provides a method for calibrating an instrument that analyzes biological samples. The method involves providing a reference solution that contains one or more analytes at known concentrations, at least two of a water soluble polymer, a glycol, and a polysaccharide, and has a conductivity that corresponds to the conductivity of a known hematocrit level, as described above. The reference solution is introduced to the instrument, and signals are obtained that represent the measured conductivity value and the concentrations of the one or more analytes. The instrument is then adjusted so that the measured conductivity value equals the known conductivity of the reference solution, and the measured concentration values equal the known concentration of the one or more analytes in the reference solution.

The foregoing and other objects, aspects, features, and advantages of the invention will become more apparent from the following description and the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 3 is a table summarizing the results of experiments that measured the hematocrit level and analyte concentrations of a reference solution according to an embodiment of the invention.

FIG. 4 is a table summarizing the results of experiments that measured the hematocrit level and analyte concentrations of aliquots of a reference solution according to an embodiment of the invention stored at different temperatures.

FIG. 5 is a table summarizing the results of experiments that measured the hematocrit level and analyte concentrations of aliquots of another reference solution according to an embodiment of the invention stored at different temperatures.

FIG. 6 is a table summarizing the results of experiments that measured the hematocrit level and analyte concentrations of aliquots of the reference solution of FIG. 5 that were pasteurized and stored at different temperatures.

DETAILED DESCRIPTION

Figure 1:
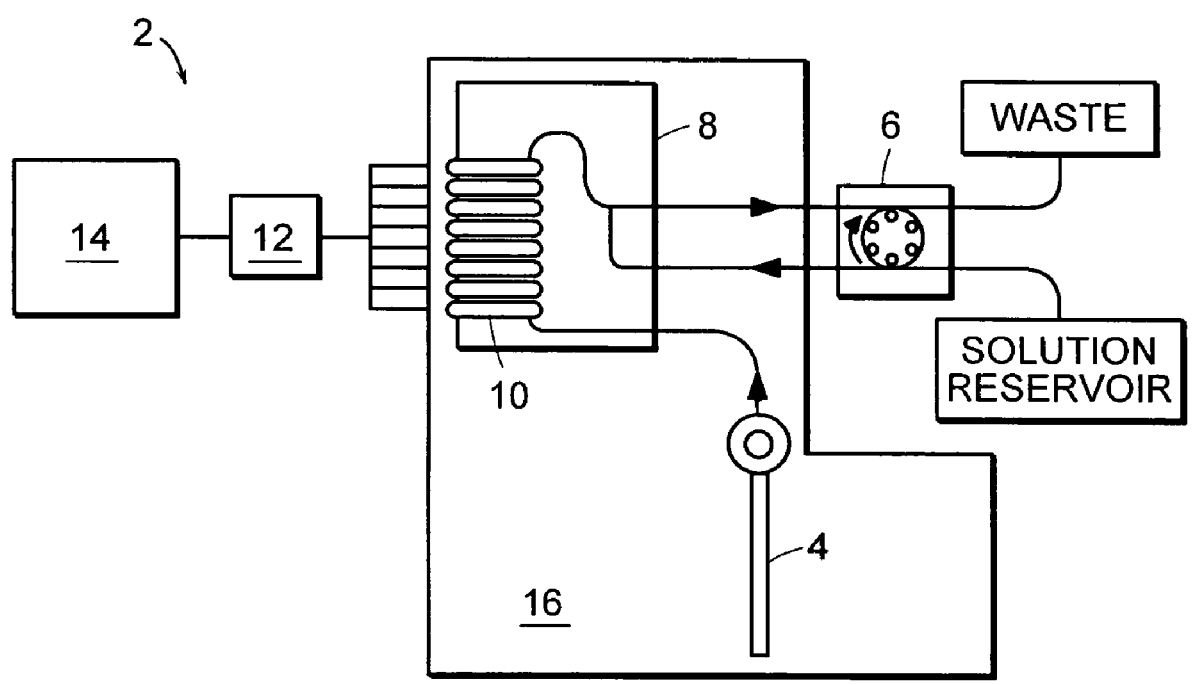
FIG. 1 is a schematic diagram of the components of an embodiment of a blood analyzer according to the invention, including a sensor cartridge with an electrode card and sample inlet, a peristaltic pump, and a microprocessor.

In general, the present invention provides a reference solution for calibrating instruments that determine hematocrit levels in biological samples. In one aspect according to the invention, the reference solution is used to calibrate an instrument that determines the hematocrit level of a blood sample (a "blood analyzer") by measuring the conductivity of the sample.

The hematocrit level (H) of a sample is related to its conductivity (C) by equation 1:

$$C = C_0(1-H) \tag{1}$$

where $C_0$ is the conductivity when H=0. A blood analyzer obtains conductivity values by measuring the resistance of a sample (where resistance R is related to conductivity C by R=1/C), then comparing the result with resistance values for two standard solutions of known conductivities. The hematocrit level of a sample ($H_x$) can be determined by measuring the resistance ($R_x$) of the sample and comparing it to the known resistance ($R_A$) and hematocrit level ($H_A$) of a standard A using equation 2:

$$R_x - R_A = R_0[(1/(1-H_x)) - 1/(1-H_A)] \tag{2}$$

where $R_0$ is the resistance when H=0.

To determine $R_0$, the resistance ($R_B$) of a second standard B having a known hematocrit level ($H_B$) must be measured. Substituting the resistance and hematocrit values for both standards A and B into equation 2 yields $R_0$. Once $R_0$ is known, the hematocrit level ($H_x$) of a sample can be determined by measuring the sample's resistance ($R_x$), and substituting the result, along with the $R_0$, $R_A$, and $H_A$ values previously determined, into equation 2.

However, the hematocrit level is not the only factor that affects the conductivity of a blood sample. For example, the conductivity of a blood sample increases as the concentration of electrolytes (such as sodium, for example) increases. Accordingly, hematocrit values determined by blood analyzers must be corrected to account for other blood components. It has been shown that correcting a measured hematocrit value for the concentration of sodium in the sample yields an accurate hematocrit value. Thus, the true hematocrit level ($H_x^*$) of a sample can be determined using equation 3:

$$1/(1-H_x^*) = [1/(1-H_x)](Na_x/Na_A) \tag{3}$$

where $Na_A$ is the sodium concentration of standard A and $Na_x$ is the sodium concentration of the sample. In a particular embodiment according to the invention, software may be included in the blood analyzer to convert resistance values measured by the analyzer to hematocrit levels by using the above equations.

In order to ensure the accuracy of hematocrit values obtained by a blood analyzer, the instrument must be calibrated with a reference solution before use, and possibly periodically during use. In one embodiment of the invention, a reference solution includes at least two of a water soluble polymer, a glycol, and a polysaccharide in such proportions to yield a solution with a conductivity that corresponds to a known hematocrit level. Examples of this embodiment include reference solutions that contain: a water soluble polymer, a glycol, and a polysaccharide; a water soluble polymer and a glycol; a water soluble polymer and a polysaccharide; and a glycol and a polysaccharide. In another embodiment of the invention, a reference solution contains a polysaccharide in such a proportion to yield a solution with a conductivity that corresponds to a known hematocrit level.

In some embodiments of the invention, the water soluble polymer is non-ionic. Examples of suitable water soluble polymers include polyethylene glycol and polyvinyl pyrrolidone, for example. The polyethylene glycol can have an average molecular weight ranging from about 1000 to about 4000, but an average molecular weight of about 2000 is preferred. Examples of suitable glycols include ethylene glycol, propylene glycol, dipropylene glycol, and glycerol, for example. In some embodiments of the invention, the polysaccharide is non-ionic. An example of a suitable non-ionic polysaccharide is dextran. The dextran can have an average molecular weight ranging from about 8000 to about 40,000, but an average molecular weight of about 10,000 is preferred.

The proper ratio of the water soluble polymer, glycol, and polysaccharide is crucial in achieving the desired conductivity of the solution, while at the same time minimizing interference with other sensors in the blood analyzer. For example, in a particular embodiment, the reference solution includes 9-15% polyethylene glycol (MW 2000), 6-10% ethylene glycol, and 6-10% dextran (MW 10,000), by weight. One example of this embodiment is a reference solution containing 90 g/L polyethylene glycol (MW 2000), 90 g/L ethylene glycol, and 60 g/L dextran (MW 10,000). Another example of this embodiment is a reference solution containing 130 g/L polyethylene glycol (MW 2000), 70 g/L ethylene glycol, and 100 g/L dextran (MW 10,000).

In another particular embodiment, the reference solution contains 7-11% polyethylene glycol (MW 2000) and 5-9% dextran (MW 10,000) by weight. One example of this embodiment is a reference solution containing 90 g/L polyethylene glycol (MW 2000) and 60 g/L dextran (MW 10,000).

In some embodiments according to the invention, the conductivity of the reference solution corresponds to a hematocrit level that falls within the range of normal human hematocrit levels. For example, in men 19 years or older, the normal range of hematocrit is between 41 and 50, while in women 19 years or older, the normal range is between 36 and 44. In other embodiments, the conductivity of the reference solution corresponds to hematocrit levels that are greater than or less than the range of normal human hematocrit levels.

In some embodiments according to the invention, the reference solution contains one or more analytes that could be found in body fluids in addition to the water soluble polymer, glycol, and polysaccharide. Examples of analytes include, but are not limited to, ions (such as hydrogen, sodium, potassium, calcium, chloride, bicarbonate, lithium, magnesium, and ammonium, for example), biological metabolites (such as glucose, lactate, urea, creatine, and creatinine, for example), and gases (such as oxygen and carbon dioxide, for example). Examples 1-3 below illustrate examples of suitable reference solution components and their respective proportions.

In other embodiments of the invention, the reference solution may contain one or more pH buffer solutions, preservatives, stabilizers, surfactants, dyes, and/or anticoagulants. Examples of a suitable pH buffers are 4-(2-hydroxyethyl)-1-piperazineethanesulfonic acid (HEPES), 3-(N-morpholino) propanesulfonic acid (MOPS), N-tris-(hydroxymethyl)methyl-2-aminoethanesulfonic acid (TES), N-tris-(hydroxymethyl)methyl glycine (TRICINE), and N,N-bis-(2-hydroxyethyl) glycine (BICINE). Preservatives include the biocide methylisothiazolinone (MIT) and formaldehyde, for example. Stabilizers serve to stabilize the other reactants in the reference solution and can include chelating or sequestering agents, for example. Examples of stabilizers include calcium chelating or sequestering agents (such as α-amino acids, α-hydroxy acids, dicarboxylic acids, and polycarboxylic acids, for example) and cations that complex with carbonate ion (such as magnesium and choline, for example). Surfactants include, but are not limited to, non-ionic surfactants. Dyes, such as food colorants, may be added in low concentrations to help identify the contents of the solution, or in high concentrations to simulate the color of hemoglobin. An example of a suitable anticoagulant is sodium heparin.

A reference solution according to the invention may be pasteurized prior to introduction to an instrument. Typical pasteurization conditions include, for example, heating to 55° C. for 16 hours, heating to 65° C. for 8 hours, heating to 75° C. for 4 hours, heating to 85° C. for 2 hours, or heating to 95° C. for 1 hour. Preferably, the solution is pasteurized after it has been added to the ampoule or container that will be introduced to the instrument. Pasteurization can stabilize a reference solution according to the invention by removing contaminants that react with oxygen and by removing neutral organic compounds that are readily oxidized to organic acids.

Another aspect of the invention provides a method for calibrating an instrument that measures hematocrit levels in biological samples obtained from a patient. The instrument may be a blood analyzer—for example, the GEM Premier 3000 manufactured by Instrumentation Laboratory Company (Lexington, Mass.)—that determines hematocrit levels in a biological sample by measuring the conductivity of the sample. Referring to FIG. 1, in one embodiment according to the invention, a blood analyzer 2 has a sample inlet 4 where the biological sample is introduced into the blood analyzer 2. A peristaltic pump 6 moves the sample through the sample inlet 4 and into an electrode card 8. The electrode card 8 contains one or more electrodes 10 that detect and measure components of interest, such as analytes, in the sample. An electrical interface 12 connects the electrode card 8 to a microprocessor 14. Signals from the electrode card 8 pass to the microprocessor 14 to allow for storage and display of the signals. Signals from the microprocessor 14 pass to the electrode card 8 to allow for control over measurement conditions, such as the polarization voltage of an electrode. In one embodiment according to the invention, the sample inlet 4 and the electrode card 8 are contained within a disposable cartridge 16, which can be detached from the remaining elements of the blood analyzer 2 and replaced after use.

Figure 2:
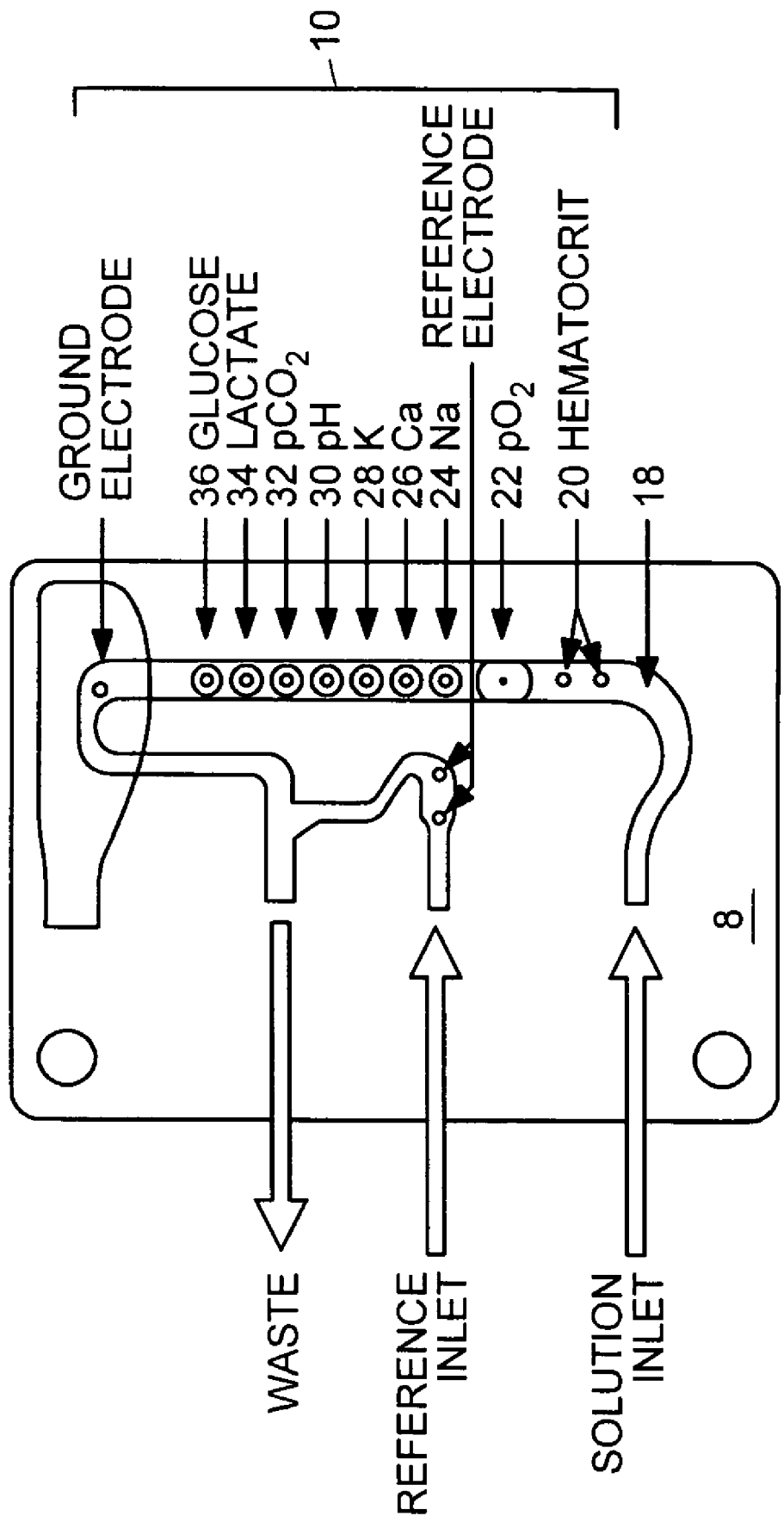
FIG. 2 illustrates a frontal view of an embodiment of an electrode card according to the invention.

Referring to FIG. 2, in one embodiment according to the invention, the electrode card 8 includes a rigid, substantially rectangular card made of polyvinyl chloride (PVC). A channel 18 is located within the electrode card 8, through which a biological sample or a reference solution may flow. One or more electrodes 10 may be embedded within the channel 18. When a sample is passed through the electrode card 8, it flows through the channel 18 and over the electrodes 10, allowing for detection and/or measurement of the components of interest.

Referring again to FIG. 2, examples of electrodes 10 that may be incorporated into the electrode card 8 include a hematocrit electrode, ion-selective electrodes, electrodes for analyzing dissolved gases, and electrodes which use an enzyme-based detection system. For example, the electrodes may detect hematocrit 20, oxygen 22, sodium 24, calcium 26, potassium 28, pH 30, carbon dioxide 32, lactate 34, and glucose 36.

Referring again to FIG. 1, in one embodiment according to the invention, a blood analyzer 2 is calibrated for hematocrit by introducing into the sample inlet 4 an embodiment of the reference solution according to the invention that includes a combination of at least two of a water soluble polymer, a glycol, and a polysaccharide in such proportions to yield a solution with a conductivity that corresponds to a known hematocrit level. The peristaltic pump 6 moves the reference solution through the sample inlet 4 and into the electrode card 8, where it comes into contact with the one or more electrodes 10. At least one of the electrodes 10 is a hematocrit electrode 20 that measures the resistance of a sample. The electrode card generates a signal based on the resistance of the sample, and the signal is transmitted to the microprocessor 14, where the corresponding hematocrit level is calculated as described above. The calculated hematocrit value is then compared against the known hematocrit value of the reference solution. If the values do not agree, the analyzer is adjusted until the calculated hematocrit value is representative of the known hematocrit value.

In one embodiment according to the invention, the method of calibration described above is repeated with a second reference solution that includes a combination of at least two of a water soluble polymer, a glycol, and a polysaccharide in such proportions to yield a solution with a conductivity that corresponds to a different known hematocrit level than the first reference solution. Additionally, the method of calibration may be repeated any number of times with reference solutions that correspond to any number of different known hematocrit levels.

Referring still to FIG. 1, in one embodiment according to the invention, a blood analyzer 2 is calibrated for hematocrit and one or more analytes by introducing into the sample inlet 4 an embodiment of the reference solution according to the invention that includes known concentrations of the one or more analytes in addition to a combination of at least two of a water soluble polymer, a glycol, and a polysaccharide in such proportions to yield a solution with a conductivity that corresponds to a known hematocrit level. As described above, the peristaltic pump 6 moves the reference solution through the sample inlet 4 and into an electrode card 8, where it comes into contact with the one or more electrodes 10. The electrodes include a hematocrit electrode 20 and at least one electrode that measures the concentration of a blood analyte in a sample. The electrode card generates a signal based on the resistance of the sample, and the signal is transmitted to the microprocessor 14, where the corresponding hematocrit level is calculated as described above. The calculated hematocrit value is then compared against the known hematocrit value of the reference solution. If the values do not agree, the analyzer is adjusted until the calculated hematocrit value is representative of the known hematocrit value. Similarly, the electrode card generates signals based on the concentrations of the analytes in the sample. The signals are transmitted to the microprocessor 14, where the measured analyte concentrations are compared against the known analyte concentrations of the reference solution. If the values do not agree, the analyzer is adjusted until the measured concentrations are representative of the known concentrations.

In one embodiment according to the invention, the method of calibration described above is repeated with a second reference solution that includes one or more analytes in addition to a combination of at least two of a water soluble polymer, a glycol, and a polysaccharide in such proportions to yield a solution with a conductivity that corresponds to a different known hematocrit level than the first reference solution. Additionally, the method of calibration may be repeated any number of times with reference solutions that correspond to any number of different known hematocrit levels.

A reference solution according to the invention can be stored in any type of container or packaging known in the art, including, but not limited to, polyethylene bottles, glass vials, glass ampoules, and foil laminate pouches. Examples of suitable containers are described in U.S. Pat. No. 6,136,607, the entire disclosure of which is incorporated by reference herein.

In addition to being used as a calibrating solution, which is used to set the response level of instrument sensors as described above, a reference solution according to the invention may be used as a control or validating solution, which is used to verify the accuracy and reliability of the instrument and the assay. The control solution is introduced to an instrument, and conductivity and/or analyte concentration values are obtained. The measured values are then compared against the known conductivity and/or concentration values to validate that the instrument and assay are performing as expected.

The following examples are intended to illustrate, but not limit, the invention.

EXAMPLE 1

A reference solution was formulated according to Table 1 below:

TABLE 1

| | |
|---|---|
| Deionized Water | 1.00 L |
| HEPES buffer | 100 mmol |
| NaOH | 75 mmol |
| NaCl | 80 mmol |
| KCl | 7.0 mmol |
| $CaCl_2$ | 1.00 mmol |
| Chloline Chloride | 1 mmol |
| Glucose | 12 mmol |
| Lithium Lactate | 4 mmol |
| MIT biocide | 2.0 mmol |
| FD&C Blue No. 1 | 0.01 g |
| FD&C Yellow No. 5 | 0.03 g |
| PEG (MW 2000) | 90 g |
| Dextran (MW 10,000) | 60 g |
| Ethylene Glycol | 90 g |

The reference solution was introduced to a blood analyzer containing an electrode card equipped with sensors to detect pH, carbon dioxide ($CO_2$), oxygen ($O_2$), sodium (Na), potassium (K), calcium (Ca), glucose (Glu), lactate (Lac), and hematocrit (Hct). Three hematocrit values were obtained, along with three concentration values for each analyte. After the final measurement, the electrode card was replaced and the procedure was repeated with a new electrode card containing the same type of electrodes. In some instances, two measurements were recorded with each electrode card, and in others one measurement was recorded. The experimental results for each of the nine analytes measured by 25 different electrode cards are summarized in FIG. 3.

FIG. 3 illustrates that the measured hematocrit levels and analyte concentrations varied only slightly among the 46 experiments. The standard deviations for the hematocrit levels and analyte concentration values were all within acceptable ranges for blood analyzing instruments. Thus, a reference solution formulated according to table 1 is effective at calibrating and/or validating a blood analyzer for pH, carbon dioxide, oxygen, sodium, potassium, calcium, glucose, lactate, and hematocrit.

EXAMPLE 2

A reference solution was formulated according to Table 2 below:

TABLE 2

| | |
|---|---|
| Deionized Water | 1.00 L |
| HEPES buffer | 100 mmol |
| NaOH | 66 mmol |
| $NaHCO_3$ | 20 mmol |
| NaCl | 68 mmol |
| KCl | 7.0 mmol |
| $CaCl_2$ | 1.00 mmol |
| Chloline Chloride | 1 mmol |
| Glucose | 12 mmol |
| Lithium Lactate | 4 mmol |
| MIT biocide | 2.0 mmol |
| FD&C Blue No. 1 | 0.01 g |
| FD&C Yellow No. 5 | 0.03 g |
| PEG (MW 2000) | 130 g |
| Dextran (MW 10,000) | 100 g |
| Ethylene Glycol | 70 g |

To predict the room temperature stability of the solution, accelerated stability studies were performed as described below.

The reference solution was introduced to a blood analyzer containing an electrode card equipped with sensors to detect pH, carbon dioxide ($CO_2$), oxygen ($O_2$), sodium (Na), potassium (K), calcium (Ca), glucose (Glu), lactate (Lac), and hematocrit (Hct). Twelve hematocrit values were obtained, along with twelve concentration values for each analyte. The average of these values is reported in the time=0 row of FIG. 4.

Aliquots of the solution were stored at 5° C., 25° C., 35° C., and 45° C. After two weeks, samples of the reference solutions stored at 5° C. and 45° C. were re-equilibrated to ambient temperature and introduced to the blood analyzer to obtain hematocrit and analyte concentration values. The procedure was repeated two additional times, yielding three sets of values for each solution. The average of these values is reported in the time=2 weeks row of FIG. 4.

The procedure was repeated at 2, 4, 6, 8, 9, 13, 16, and 20 weeks for the solution stored at 5° C. For the aliquots stored at elevated temperatures, once the value for any analyte deviated from the time=0 value by more than 1.5 times the acceptable range, testing on the solution was halted and the next lower temperature was tested. Accordingly, the reference solution stored at 45° C. was tested at 2 and 4 weeks, the 35° C. solution was tested at 4, 6, and 8 weeks, and the 25° C. solution was tested at 9, 13, 16, and 20 weeks. The results of these experiments are summarized in FIG. 4.

The projected room temperature shelf life of the solution was determined from the data in FIG. 4 by comparing the hematocrit and analyte concentration values at each time-point against the values at t=0 for the solution stored at 25° C. As shown in FIG. 4, the $pO_2$ value obtained for the solution stored at 25° C. was within the acceptable range (±5 mmHg) at 13 weeks (122 mmHg), but was outside the range at 16 weeks (109 mmHg). Thus, 13 weeks represents a conservative estimate of room temperature shelf-life for the solution.

Second, the predicted shelf life of the solution stored at 5° C. was estimated using the "10° C. rule." The change in $pO_2$ values for each of the solutions stored at 25° C., 35° C., and 45° C. were plotted against time, and the time-to-failure (i.e., the point at which the $pO_2$ value fell outside the acceptable range) was determined for each temperature. The ratio of the time-to-failure values between 35° C. (3.52 weeks) and 45° C. (0.83 weeks) was 4.2, and the ratio between 25° C. (13.5 weeks) and 35° C. (3.52 weeks) was 3.8, yielding an average time-to-failure ratio of 4.0 for each 10° C. change in temperature. In other words, for every 10° C. change in storage temperature, the time-to-failure for the solution changes by a factor of four. Thus, the predicted time-to-failure of the solution stored at 5° C. is 216 weeks, based on a time-to-failure value of 13.5 weeks for the solution stored at 25° C.

EXAMPLE 3

A reference solution was formulated according to Table 3 below:

TABLE 3

| Deionized Water | 1.00 L |
|---|---|
| HEPES buffer | 100 mmol |
| NaOH | 44 mmol |
| $NaHCO_3$ | 20 mmol |
| NaCl | 58 mmol |
| KCl | 3.0 mmol |
| $CaCl_2$ | 2.00 mmol |
| Chloline Chloride | 1 mmol |
| Glucose | 3 mmol |
| Lithium Lactate | 0.8 mmol |

TABLE 3-continued

| MIT biocide | 2.0 mmol |
|---|---|
| FD&C Blue No. 1 | 0.05 g |
| PEG (MW 2000) | 90 g |
| Dextran (MW 10,000) | 60 g |

Accelerated stability studies on the solution were conducted as described above. First, aliquots of the solution stored at 5° C. and 25° C. were tested as above at 4, 6, and 12 weeks. The results of this study are summarized in FIG. 5. After 12 weeks, no appreciable change in hematocrit and analyte concentration values were recorded, so the test was halted. New aliquots of the solution were placed in ampoules and pasteurized. An accelerated stability study was performed, as described above, on aliquots stored at 5° C., 35° C., and 45° C. After 4 weeks, no appreciable change in hematocrit and analyte concentration values were recorded, as shown in FIG. 6. The results of these two experiments indicate that a reference solution formulated according to table 3 is an effective calibrating and/or validating solution for pH, carbon dioxide, oxygen, sodium, potassium, calcium, glucose, lactate, and hematocrit, and has an acceptable shelf-life.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A reference solution for use in instruments that analyze biological samples, comprising 7-15% of a water soluble polymer by weight, 6-10% of a glycol by weight, and 5-10% of a polysaccharide by weight, wherein the reference solution has a conductivity corresponding to a known hematocrit level of a blood sample.

2. The reference solution according to claim 1, wherein the water soluble polymer is non-ionic.

3. The reference solution according to claim 2, further comprising one or more analytes.

4. The reference solution according to claim 1, wherein the water soluble polymer is polyethylene glycol.

5. The reference solution according to claim 1, wherein the glycol comprises at least one glycol selected from the group consisting of ethylene glycol, propylene glycol, dipropylene glycol, and glycerol.

6. The reference solution according to claim 1, wherein the glycol is ethylene glycol.

7. The reference solution according to claim 1, wherein the polysaccharide is non-ionic.

8. The reference solution according to claim 1, wherein the polysaccharide is dextran.

9. The method of claim 8, wherein the dextran has a molecular weight ranging from about 8,000 to about 40,000.

10. The reference solution according to claim 1, further comprising at least one analyte.

11. There reference solution according to claim 10, wherein the analyte comprises an ion.

12. The reference solution according to claim 11, wherein the ion is selected from the group consisting of hydrogen, sodium, potassium, calcium, chloride, bicarbonate, lithium, magnesium, and ammonium.

13. The reference solution according to claim 11, wherein the concentration of the ion in the reference solution corresponds to the physiological concentration of the ion in human blood.

14. The reference solution according to claim 10, wherein the analyte comprises a biological metabolite.

15. The reference solution according to claim 14, wherein the biological metabolite is selected from the group consisting of glucose, lactate, urea, creatine, and creatinine.

16. The reference solution according to claim 14, wherein the concentration of the biological metabolite in the reference solution corresponds to the physiological concentration of the biological metabolite in human blood.

17. The reference solution according to claim 10, wherein the analyte comprises a gas.

18. The reference solution according to claim 17, wherein the gas is selected from the group consisting of oxygen and carbon dioxide.

19. The reference solution according to claim 17, wherein the partial pressure of the gas in the reference solution corresponds to the physiological partial pressure of the gas in human blood.

20. The reference solution according to claim 1, further comprising one or more additives selected from the group consisting of pH buffer solutions, preservatives, stabilizers, surfactants, dyes, and anticoagulants.

21. The reference solution according to claim 1, wherein the hematocrit level corresponds to the physiological hematocrit level in human blood.

22. The reference solution according to claim 1, wherein the hematocrit level is greater than the physiological hematocrit level in human blood.

23. The reference solution according to claim 1, wherein the hematocrit level is less than the physiological hematocrit level in human blood.

24. The reference solution according to claim 1, wherein the biological sample comprises blood.

25. A reference solution for use in instruments that analyze biological samples, comprising:
   7-15% polyethylene glycol by weight,
   6-10% ethylene glycol by weight, and
   5-10% dextran by weight,
   wherein the reference solution has a conductivity corresponding to a known hematocrit level of a blood sample.

26. The reference solution according to claim 25, further comprising one or more analytes.

27. The method of claim 25, wherein the dextran has a molecular weight ranging from about 8,000 to about 40,000.

28. A reference solution for use in instruments that analyze biological samples, comprising:
   7-11% polyethylene glycol by weight and 5-9% dextran by weight, wherein the dextran has a molecular weight ranging from about 8,000 to about 40,000 and wherein the reference solution has a conductivity corresponding to a known hematocrit level of a blood sample.

29. A method of calibrating an instrument that analyzes biological samples, comprising:
   (a) introducing a reference solution to the instrument, the reference solution comprising a water soluble polymer, a glycol, and a polysaccharide, wherein the reference solution has a conductivity corresponding to a known hematocrit level of a blood sample;
   (b) obtaining a signal from the instrument corresponding to a conductivity of the reference solution; and
   (c) adjusting the instrument so that the signal obtained from the instrument is representative of the conductivity corresponding to the known hematocrit level.

30. The method according to claim 29, further comprising:
   (d) obtaining a signal from the instrument corresponding to a conductivity of a known concentrations of one or more analytes in the reference solution; and
   (e) adjusting the instrument so that the signal obtained from the instrument is representative of the conductivity corresponding to the known concentrations of the one or more analytes.

* * * * *